(12) United States Patent
Rüdinger et al.

(10) Patent No.: US 6,884,909 B2
(45) Date of Patent: Apr. 26, 2005

(54) PROCESS FOR PREPARING SATURATED CARBOXYLIC ACIDS HAVING FROM ONE TO FOUR CARBON ATOMS BY GAS-PHASE OXIDATION OF 2-BUTANONE

(75) Inventors: Christoph Rüdinger, Starnberg (DE); Harald Herbert Voit, Reischach (DE); Hans-Jürgen Eberle, München (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 10/285,206

(22) Filed: Oct. 31, 2002

(65) Prior Publication Data

US 2003/0114709 A1 Jun. 19, 2003

(30) Foreign Application Priority Data

Dec. 6, 2001 (DE) .......................................... 101 59 834

(51) Int. Cl.[7] ........................ C07C 51/245; C07C 53/08; C07B 53/00

(52) U.S. Cl. ........................ 562/527; 562/606; 562/607

(58) Field of Search ................................ 562/527, 606, 562/607

(56) References Cited

U.S. PATENT DOCUMENTS

| | | | |
|---|---|---|---|
| 3,431,297 A | 3/1969 | Brockhaus | |
| 3,627,823 A | 12/1971 | Brockhaus et al. | |
| 3,917,682 A | 11/1975 | Mizukami et al. | |
| 3,954,857 A | 5/1976 | Brockhaus | |
| 4,146,734 A | 3/1979 | Slinkard | |
| 4,448,892 A | 5/1984 | Kukes et al. | |
| 4,448,897 A | 5/1984 | Gastinger | |
| 4,550,212 A | 10/1985 | Shioyama | |
| 6,274,763 B1 | 8/2001 | Ruedinger et al. | |
| 6,320,075 B1 * | 11/2001 | Ruedinger et al. | .......... 562/549 |

FOREIGN PATENT DOCUMENTS

| | | |
|---|---|---|
| DE | 1 049 845 | 8/1959 |
| DE | 1 643 824 | 11/1967 |
| DE | 1 279 011 | 10/1968 |
| DE | 2026 744 | 4/1971 |
| DE | 1 643 822 | 5/1971 |

(Continued)

OTHER PUBLICATIONS

English Derwent Abstract AN 1976–30255x corresponding to DE 25 25 296.
English Derwent Abstract AN 1970–58322 R [33] corresponding to DE 1 643 824.
English Derwent Abstract AN 1971–67471S [42] corresponding to DE 2016681.
English Derwent Abstract AN 1974–11613V [07] corresponding to DE 22 35 103.
English Derwent Abstract AN 1998–313425 [28] corresponding to EP 951 351.
English Derwent Abstract AN 2000–014559 [02] corresponding to EP 960874.
English Derwent Abstract AN 2000–001435 [01] corresponding to EP 960875.

(Continued)

*Primary Examiner*—Paul A. Zucker
(74) *Attorney, Agent, or Firm*—Collard & Roe, P.C.

(57) ABSTRACT

A process for preparing saturated carboxylic acids having from one to four carbon atoms by gas-phase oxidation, includes reacting 2-butanone with oxygen over a coated catalyst which is an inert nonporous support body and a catalytically active mixed oxide composition comprising (a) one or more oxides selected from the group consisting of titanium dioxide, zirconium dioxide, tin dioxide and aluminum oxide, and (b) from 0.1% to 1.5% by weight, based on the weight of the component (a) and per $m^2/g$ of specific surface area of the component (a), of vanadium pentoxide, applied to the external surface of the support body.

20 Claims, 2 Drawing Sheets

FOREIGN PATENT DOCUMENTS

| | | |
|---|---|---|
| DE | 2 016 681 | 10/1971 |
| DE | 2 110876 | 10/1971 |
| DE | 2525296 | 4/1976 |
| DE | 22 35 103 | 4/1978 |
| DE | 2354425 | 5/1978 |
| DE | 196 49 426 | 6/1998 |
| DE | 199 34 410 | 12/2000 |
| DE | WO 01/073390 A1 * | 2/2001 |
| DE | 199 34 411 | 3/2001 |
| DE | 10065 466 | 7/2002 |
| EP | 498305 | 8/1992 |
| EP | 960874 | 12/1999 |
| EP | 960875 | 12/1999 |
| EP | 1 035 101 | 9/2000 |
| EP | 951 351 | 5/2001 |
| EP | 1 108 470 | 6/2001 |
| GB | 1 333 306 | 10/1973 |
| WO | 98/23371 | 6/1998 |

OTHER PUBLICATIONS

English Derwent Abstract AN 2002–599598 [64] corresponding to DE 100 65 466.
English Derwent Abstract AN 2000–551170 [51] corresponding to EP 1035101.
English Derwent Abstract AN 2001–504086 [56] corresponding to EP 1108470.
English Derwent Abstract AN 2001–008701 [02] corresponding to DE 199 34 410.
English Derwent Abstract AN 2001–191355 [19] corresponding to DE 19934411.
English Derwent Abstract AN 1998–313425 [28] corresponding to DE 196 49 426.

* cited by examiner

PROCESS FOR PREPARING SATURATED CARBOXYLIC ACIDS HAVING FROM ONE TO FOUR CARBON ATOMS BY GAS-PHASE OXIDATION OF 2-BUTANONE

BACKGROUND OF THE INVENTION

1. Field of the Invention

The present invention relates to a process for preparing saturated carboxylic acids having from one to four carbon atoms, in particular acetic acid, by gas-phase oxidation of 2-butanone using a coated catalyst.

2. The Prior Art

It is known that saturated carboxylic acids having from one to four carbon atoms and in particular acetic acid can be prepared by gas-phase oxidation of short-chain aliphatic compounds, particularly butenes and alcoholic or ketonic oxidation products obtainable therefrom, by means of a catalyst. However, no process which is fully satisfactory from economic and production engineering points of view has been found hitherto.

DE-1 643 822 C3 describes a process for preparing acetic acid by catalytic gas-phase oxidation of short-chain aliphatic compounds by means of oxygen using aluminum vanadate and titanium vanadate catalysts. These catalysts are prepared by precipitation of the mixed oxides from the corresponding solutions and are used as granulated all-active catalysts. Disadvantages of these catalysts are the high degree of total oxidation and the difficulty of controlling heat removal. As a result, a yield of only 75% and a maximum acetic acid production of 64 g per liter of catalyst and hour are achieved in the prior art oxidation of methyl ethyl ketone (2-butanone). Furthermore, a crude acid having a concentration of only about 12% by weight is obtained. This requires a very costly concentration and purification in order to obtain a commercial >99% strength pure acetic acid.

DE-1 643 824 C describes a process for preparing concentrated acetic acid by catalytic gas-phase oxidation of butenes and alcoholic or ketonic oxidation products obtainable therefrom. The catalysts used are aluminum vanadate, antimony vanadate, tin vanadate and titanium vanadate catalysts in a sequence of individual reactors connected in series. These catalysts are prepared by precipitation of the mixed oxides from the corresponding solutions and are used as granulated all-active catalysts. Disadvantages of this process and the catalysts described therein are the high degree of total oxidation and the difficulty of controlling heat removal. As a result a yield of only 66% and a maximum acetic acid production of 126 g per liter of catalyst and hour are achieved in the prior art oxidation of methyl ethyl ketone (2-butanone). Furthermore, a crude acid having a maximum concentration of only 34% by weight is obtained. This requires, in addition to the very complex series arrangement of four reactors having their own introduction of starting material and two condensers, very costly concentration and purification of the crude acid in order to obtain a commercial >99% strength pure acetic acid.

DE-1 643 824 C describes the use of 2-butanone (methyl ethyl ketone) as a starting material which gives poorer results with respect to the acetic acid yield and the achievable space-time yield. It also describes the poorer results for the crude acid concentration compared to the use of n-butenes such as 1-butene, trans-2-butene, cis-2-butene.

DE-1279011 B describes a process for preparing acetic acid by catalytic gas-phase oxidation of butene by means of oxygen using aluminum vanadate and titanium vanadate catalysts. These catalysts are likewise prepared by precipitation of the mixed oxides from the corresponding solutions, with the mixed oxides being able, if desired, to be mixed with inert materials such as silica. The catalyst is used as a finely divided powder in fluidized-bed reactors. A disadvantage of such all-active catalysts is the high degree of total oxidation.

To improve the yield obtained using such catalysts, DE-2016681 A proposes that the catalysts be treated with an oxidant prior to calcination. DE-A 2354425 C3 (U.S. Pat. No. 3,954,857) proposes treatment of the calcined titanium-vanadium mixed catalyst with hydrochloric acid to improve the selectivity. The catalysts are used as all-active catalysts, if desired in admixture with inert support materials such as silica.

A further starting point known from the prior art for improving the activity of titanium-vanadium mixed catalysts in the gas-phase oxidation of butenes to acetic acid is the use of titanium dioxide in a defined crystal form or with a defined surface area. DE-A 2026744 (U.S. Pat. No. 3,917,682) describes titanium-vanadium mixed catalysts whose titanium dioxide component is predominantly present as rutile. The catalysts can be used in powder form or as pressed shaped bodies. U.S. Pat. No. 4,448,897 discloses Ti-vanadium catalysts comprising titanium dioxide having a BET surface area of greater than 40 $m^2/g$ for butene oxidation. The catalysts are likewise used in powder form or as pressed bodies.

It is also known from the prior art that the selectivity of titanium-vanadium catalysts in the oxidation of butenes can be improved by replacing all or part of the titanium dioxide present by other metal oxides. DE 2110876 A (GB 1333306), for example, describes catalysts comprising oxides of molybdenum, tin and vanadium as active components. The catalysts are used in powder form, and the mixed oxide catalyst can, if desired, also be applied to finely divided support materials such as silicon dioxide. U.S. Pat. No. 4,146,734 discloses the use of vanadium mixed oxides doped with cerium and further transition metal oxides. The catalyst is used as fine granules but can also be applied as a precipitate to finely divided, inert supports.

DE 2235103 C3 discloses titanium-vanadium mixed oxide catalysts for the gas-phase oxidation of butenes in the form of supported catalysts obtained by impregnating a previous shaped porous support with the mixed solution of the catalyst components.

All these catalysts are all-active catalysts in which the active components themselves are used as powder or pressed bodies, or are diluted with finely divided support materials before use as powder or pressed bodies. For the purposes of the present invention, all-active catalysts also include porous supports impregnated right through with an active component as described in DE 2235103 C3, since here, too, the total catalyst volume is catalytically active.

Disadvantages of all these processes and catalysts are the high degree of total oxidation, the difficulty of controlling the oxidation reaction at high space-time yields and the low acetic acid concentration in the crude acid. These disadvantages lead to high production costs for the acetic acid.

EP 0 951 351 and EP 0 960 874 describe a coated catalyst for preparing acetic acid by gas-phase oxidation of hydrocarbons having four carbon atoms ($C_4$-hydrocarbons).

EP 0 960 875 and EP 1 035 101 describe processes for preparing saturated carboxylic acids having from 1 to 4 carbon atoms from saturated and unsaturated $C_4$-hydrocarbons using coated catalysts.

These processes have the disadvantage that although high acetic acid yields are achieved, the volume-based acetic acid productivity (space-time yield) and the concentration of the crude acid are not fully satisfactory. Consequently, implementation of these processes is still associated with high reactor and work-up costs.

It has also been found that increasing the proportion of n-butenes in the raw material or increasing the reactor throughput enables the volume-specific acetic acid productivity of the known processes for producing acetic acid from $C_4$-hydrocarbon mixtures to be increased only insignificantly and/or with reductions in selectivity.

SUMMARY OF THE INVENTION

It is therefore an object of the present invention to provide a process for preparing saturated carboxylic acids having from one to four carbon atoms, in particular acetic acid, by gas-phase oxidation, which process avoids the disadvantages of the prior art.

It has surprisingly been found that the above object is achieved by the present invention wherein the preparation of saturated carboxylic acids having from one to four carbon atoms, in particular acetic acid, by gas-phase oxidation is particularly economical when coated catalysts in which the active composition has been applied as a thin layer to a nonporous support body are used and a 2-butanone-containing starting material is employed.

The present invention provides a process for preparing saturated carboxylic acids having from one to four carbon atoms by gas-phase oxidation, which comprises reacting 2-butanone with oxygen in contact with a coated catalyst comprising an inert nonporous support body and a catalytically active mixed oxide composition comprising
a) one or more oxides selected from the group consisting of titanium dioxide, zirconium dioxide, tin dioxide and aluminum oxide, and
b) from 0.1 to 1.5% by weight, based on the weight of the component a) and per $m^2/g$ of specific surface area of the component a), of vanadium pentoxide,
applied to an external surface of the support body.

In contrast to the processes known from the prior art, the process of the invention has the following advantages. This process gives high acid yields and thus good utilization of raw material, high crude acid concentrations which result in low work-up costs and at the same time an increased volume-based acid productivity (high space-time yield) which is in turn reflected in lower plant costs.

The process of the present invention is suitable for preparing saturated carboxylic acids having from one to four carbon atoms, preferably for preparing acetic acid and formic acid, particularly preferably acetic acid. A significant advantage of the procedure according to the invention is that in the preparation of acetic acid, the by-products formed in small amounts are obtained as materials of value, especially in the form of formic acid. In contrast, in the processes known from the prior art, especially those using all-active catalysts, the formic acid formed as an intermediate is decomposed to form $CO_x$ compounds which have to be disposed of by incineration.

2-Butanone is a readily available chemical which is produced on a large scale. 2-Butanone is usually obtained by oxidation of hydrocarbons in the liquid phase, hydration of n-butenes and dehydrogenation of the resulting 2-butanol to 2-butanone or via a direct oxidation of n-butenes by means of oxygen over palladium catalysts in the liquid phase to give 2-butanone. The latter process is closely related to the preparation of acetaldehyde from ethylene by direct oxidation by means of oxygen over palladium catalysts in the liquid phase.

The process of the present invention is equally suitable for using pure 2-butanone, 2-butanone-containing mixtures and/or 2-butanone-containing crude products from various production processes for 2-butanone as feedstock and thus as carbon source for the gas-phase oxidation.

Since the preparation of acetic acid from ethylene via acetaldehyde has become uninteresting from an economic point of view because of the high raw material cost of ethylene, a change from the expensive raw material basis of ethylene to the cheap raw material basis of n-butenes has become particularly attractive. This is in addition to other alternative processes which have been described for the preparation of acetic acid.

In a preferred embodiment of the present invention, n-butenes are converted into 2-butanone by means of a direct oxidation process known from the prior art, as is described, for example, in DE 1049845 B, EP 0498 305, U.S. Pat. No. 4,448,892 or U.S. Pat. No. 4,550,212. The 2-butanone-containing product mixtures obtained from the processes without further work-up can be used directly as feedstocks in the process of the invention. The further direct conversion of these primary product mixtures from the preparation of 2-butanone into acetic acid is of particular economic interest because a work-up is not necessary.

Small amounts of water and unreacted starting materials and by-products from the direct oxidation of n-butenes which are present in the feedstock in addition to 2-butanone do not cause problems in the process of the invention.

The insensitivity of the process of the invention to any other materials or mixtures present in the 2-butanone feedstock allows very inexpensive preparation of a 2-butanone-containing raw material mixture suitable for the process of the invention using a known direct oxidation process over palladium catalysts.

In a particularly preferred embodiment of the present invention, the water/2-butanone azeotropes formed initially as crude products in a process known from the prior art for the direct oxidation of 2-butenes over palladium catalysts are used as 2-butanone feedstock. Costly dewatering of the initially obtained water/2-butanone azeotrope is not necessary. Even the by-products of the reaction, particularly the butyraldehyde which is difficult to separate off because of its similar boiling point, and residual unreacted starting materials do not have to be separated off, which would be costly.

When existing acetic acid plants using the Wacker/Hoechst process employing ethene as raw material basis are converted to butene mixtures as raw material basis, part of the existing plant can be utilized further.

For the cost-competitive preparation of 2-butanone, preference is given to using inexpensive raw material mixtures from the petrochemicals industry. Examples of these mixtures include "$C_4$ fraction" (predominantly butadiene and i-butene), "raffinate 1" (predominantly i-butene and n-butenes) and "raffinate 2" (predominantly butanes, 1-butene and 2-butenes), or mixtures comprising such hydrocarbons as starting material, if appropriate after a pretreatment, e.g. a purification or hydrogenation.

The reaction temperature of the gas-phase oxidation is generally from 100° C. to 400° C., preferably from 150° C. to 300° C., particularly preferably from 180° C. to 250° C.

The reaction is generally carried out at pressures of from $1.2 \times 10^5$ to $51 \times 10^5$ Pa, preferably from $4 \times 10^5$ to $41 \times 10^5$ Pa, particularly preferably from $9 \times 10^5$ to $17 \times 10^5$ Pa.

Suitable catalysts for the process of the invention are all catalysts which have been described generally for the partial oxidation of saturated and/or unsaturated $C_4$-hydrocarbons to acetic acid. Preference is given to mixed oxide catalysts which comprise vanadium oxides. Particular preference is given to coated catalysts comprising an inert nonporous support body and a catalytically active mixed oxide composition comprising a) one or more oxides selected from the group consisting of titanium dioxide, zirconium dioxide, tin dioxide and aluminum oxide, and b) from 0.1 to 1.5 by weight, based on the weight of the component a) and per $m^2/g$ of specific surface area of the component a), of vanadium pentoxide, applied to the external surface of the support body.

In addition, the component a) can further comprise one or more oxides of metals selected from the group consisting of boron, silicon, hafnium, niobium, tungsten, lanthanum and cerium. When the component a) is doped with the oxides mentioned, these are generally present in an amount of from 1 to 30% by weight, based on the total weight of the component a).

In the component b), part of the vanadium pentoxide, preferably from 10 to 90% by weight, can be replaced by one or more oxides of molybdenum, chromium and antimony, and/or one or more oxides of alkali metals, alkaline earth metals, elements of main groups 5 and 6 of the Periodic Table of the Elements and the transition metals may also be present as additional component b). In general, the amount of these dopants is from 0.005 to 15% by weight, calculated as oxides and based on the total weight of the component b).

Preference is given to compositions having a high surface area of the component a) of from 40 to 300 $m^2/g$, in which tin oxide, niobium oxide or tungsten oxide may additionally be present, together with a component b) which is doped with Mo and/or Cr and/or Sb and/or Au.

The catalytically active mixed oxide composition can, if desired, further comprise from 10 to 50% by weight, based on the total weight of the catalytically active mixed oxide composition, of inert diluents selected from the group consisting of silicon dioxide, silicon carbide and graphite.

The catalytically active mixed oxide composition is preferably applied in an amount of from 1% to 40% by weight, preferably from 5% to 25% by weight, in each case based on the total weight of support body and active composition, as a shell to the external surface of the support body.

The thickness of the layer is preferably from 10 to 2000 $\mu$m, in particular from 100 to 1000 $\mu$m. The coated catalyst can also have a plurality of layers having different compositions. It is also possible for one or more constituents of the active components (a) and (b) to be present in different concentrations in the individual layers. In a further embodiment, the inner layer comprises only the component (a) and the outer layer comprises the components (a) and b). One conceivable embodiment is a multilayer coated catalyst in which the inner layer and the outer layer each comprise the components (a) and (b) and a higher specific surface area of the component a) is selected for the inner layer than for the outer layer.

Suitable materials for the inert, nonporous support body are generally all nonporous materials which are inert under the operating conditions of the gas-phase oxidation and are stable for the period of operation. Examples are steatite, duranite, silicon carbide, magnesium oxide, silicon oxide, silicates, aluminates, metals such as stainless steel, and also, if appropriate, mixtures of these materials. Preference is given to ceramic materials such as steatite.

The inert, nonporous support body of the coated catalyst can have any shape. Examples of suitable shapes are spheres, cylinders, hollow cylinders, cuboids, tori, saddles, spindles, helices. The basic bodies can also have one or more recesses such as depressions, grooves, holes, or else projecting parts such as pins, points, fins. Further examples are rings, segments of rings, finned rings, spheres with a hole through the middle, segments of spheres. Ordered packing elements such as monoliths or cross-channel structures are likewise suitable as supports. Preference is given to support shapes having a very high geometric surface area per unit volume, for example rings or hollow cylinders. In a particularly preferred embodiment, the inert support bodies have the shape of hollow cylinders which have one or more notches on the upper and/or lower end face of the hollow cylinder walls, so that the interior space of the hollow cylinders is joined to the spaces surrounding the hollow cylinders via openings.

The dimensions of the support bodies are generally determined by the reactors employed for the gas-phase oxidation. The shaped bodies preferably have a length and/or diameter of from 2 to 20 mm. The wall thickness, for example in the case of rings or hollow cylinders, is advantageously from 0.1 to 4 mm.

Further details of preferred embodiments of the catalysts are described in EP 095135, EP 0960874 and EP 1108470, whose relevant disclosures are incorporated by reference into the present patent application.

As reactors for carrying out the process of the invention, it is generally possible to use designs which are suitable for carrying out oxidation reactions in the gas phase and are able to remove the high heat of reaction without excessive heating of the reaction mixture. The process of the invention can be carried out continuously or intermittently, i.e. the reactor inlet mixture can be fed in at a constant feed rate or with a cyclically varying feed composition. The gas mixture can preferably react over the catalyst in a fixed bed, for example by contacting the catalyst in a shell-and-tube reactor or a tray reactor, or in a moving or fluidized bed. Particular preference is given to cooled shell-and-tube reactors containing a fixed catalyst bed. Particular preference is given to designs having individual tubes which have an internal tube diameter of from 10 mm to 50 mm and a tube length of from 1 m to 6 m arranged as bundles.

The flow velocity, based on the empty tube, in the reaction tubes is generally from 0.1 m/s to 10 m/s, preferably from 0.3 m/s to 5 m/s, particularly preferably from 0.5 to 3 m/s.

The reaction tubes can be charged with catalysts of differing compositions, shapes and dimensions. The charge is preferably introduced homogeneously or variably in zones in an axial direction into the reaction tubes. Each zone preferably contains a randomly diluted or mixed catalyst.

The oxygen source necessary for the gas-phase oxidation is generally an oxygen-containing gas. As oxygen-containing gas, preference is given to using air, more preferably oxygen-enriched air and particularly preferably pure oxygen. However, an inert gas, preferably nitrogen and/or argon, can additionally be present in the process of the invention.

The oxygen content of the inlet gas stream fed into the reactor is preferably from 1% to 35% by volume, particularly preferably from 3% to 20% by volume, in particular from 4% to 12% by volume. The percent by volume is based upon the total inlet gas volume.

If desired, a proportion of inert gas of the inlet gas stream is from 0% to 25% by volume can be introduced. The percent by volume is based upon the total inlet gas volume.

The proportion by volume of water vapor in the reactor inlet gas stream fed to the reactor is generally from 5% to 80% by volume, preferably from 5% to 40% by volume, particularly preferably from 5% to 30% by volume. The percent by volume is based upon the total inlet gas volume.

The proportion of 2-butanone in the reaction inlet gas, measured at the reactor inlet, is preferably from 0.3% to 10% by volume, particularly preferably from 0.5% to 3.0% by volume. The percent by volume is based upon the total inlet gas volume.

In a preferred embodiment of the invention, the process of the invention is carried out with gas recirculation as a circulation process. In processes with gas recirculation, the proportion of carbon oxides and further reaction by-products in the reactor inlet gas depends on the way in which the reaction is carried out and the separation of acid. It is generally from 0% to 90% by volume, preferably from 10% to 90% by volume, particularly preferably from 50% to 80% by volume. The percent by volume is based upon the total inlet gas volume.

The percentages by volume of the individual constituents of the reactor inlet gas in each case add up to 100% by volume.

As apparatus for carrying out the reaction of the invention, it is generally possible to use apparatuses in which the gas makes a single pass through the reactor and circulation processes. In the case of circulation processes, preference is given to apparatuses in which high boilers such as the carboxylic acids acetic and formic acid compared to the low boilers such as unreacted ketones and low-boiling intermediates and by-products are preferably separated off from the recirculated gas stream. The crude acid from the reactor outlet gas is preferably separated off by means of a countercurrent scrub, a cocurrent scrub, a cross-stream scrub, quench cooling, partial condensation or a combination of these methods. Further details of preferred embodiments are described in EP 0960875 and EP 1035101, whose relevant disclosures are herewith incorporated by reference into the present patent application.

In a particularly advantageous embodiment of the invention, the reaction gas circuit is configured so that part of the organic acids formed in the gas-phase oxidation, primarily acetic acid and formic acid, are separated off from the reactor outlet gas, i.e. the gas mixture leaving the reactor or the recirculated gas mixture. This is done by means of a partial condenser or a countercurrent scrub using a suitable solvent, preferably water, a proportion of acids and other compounds. The separation is carried out so that the partial pressure of these acids remains low at the reactor inlet and unreacted 2-butanone and intermediates which can be reacted further, e.g. acetaldehyde, acetone, methyl acetate, 2-butanol, etc., mostly remain in the circulating gas and are recirculated to the reactor inlet.

A possible procedure is to separate off the acids from part of the reactor outlet gas, in general from 60% to 99.8% by weight, preferably from 90% to 99.5% by weight, to leave the abovementioned residual acid content and subsequently to return this part of the reactor outlet gas to the reactor. The untreated part of the reactor outlet gas is discarded and can, for example, be flared. The proportion of untreated reactor outlet gas depends on the amount of carbon oxides $CO_x$ which has been formed, because these have to be removed via this bleed stream. They can then be disposed of by incineration. Each percent by weight is based upon the total weight of the reactor outlet gas.

Another possible procedure is to separate off the acids down to the abovementioned residual content from the reactor outlet gas immediately after it leaves the reactor and to recirculate all or part, preferably from 60% to 99.8% by weight, particularly preferably from 90% to 99.5% by weight, of the reactor outlet gas which has been treated in this way to the reactor. This embodiment is particularly preferred since the target products, viz. the carboxylic acids, are largely separated off beforehand and do not go to incineration. Each percent by weight is based upon the total weight of the reactor outlet gas.

The mass flow of recirculated gas is generally from 1 to 100 times, preferably from 10 to 80 times, particularly preferably from 30 to 60 times, the mass flow of fresh feed introduced.

The water vapor content of the gas stream leaving the absorber is generally determined by the temperature prevailing at the absorber outlet and the operating pressure. The temperature is generally determined by the amount of heat removed from the absorber and the amount and temperature of the scrubbing water stream and is generally from 50° C. to 200° C. The residual acid content of the gas stream leaving the absorber is generally determined by the pressure and temperature, the number of theoretical plates of the absorber and the amount of absorption medium introduced (water feed). In general, the process is carried out so that the countercurrent scrub reduces the residual acid concentration of the gas stream recirculated to the reactor to from 0.01% to 12% by volume, preferably from 0.1% to 8% by volume. The percent by volume is based upon the total gas stream recirculated volume.

The water obtained in the concentration and purification of the crude acid is partly, if appropriate after chemical and/or physical treatment, fed back into the countercurrent absorption, so that very little wastewater is produced in the overall process.

The crude acid which has been separated off is generally dewatered and purified using suitable customary processes either alone or in combination, e.g. liquid/liquid extraction, extractive rectification, azeotropic rectification, rectification, crystallization and membrane separation processes. The low boilers which have been separated off before further fractionation of the crude acid into its pure substances can likewise, either alone or together with low boilers from the purification and concentration, be recirculated wholly or partly to the gas-phase reactor.

Processes which are particularly suitable for the work-up of the dilute crude acid are processes which have been optimized in terms of costs, as are described in DE 199 34 411 C1, DE 199 34 410 C1 and the German patent application DE 10065466, whose relevant disclosures are hereby incorporated by reference into the present patent application.

A preferred method of separating and purifying the dilute crude acid, viz. an aqueous mixture of the main components acetic acid, formic acid and high boilers, is extraction by means of a solvent. Preferably this solvent includes one or more compounds selected from the group consisting of ethers, esters, ketones and alcohols, particularly preferably one or more compounds selected from the group consisting of methyl tert-butyl ether, diisopropyl ether, ethyl butyl ether, ethyl acetate and isopropyl acetate, in a circulation process, wherein the raffinate stream containing the major part of the water is fed to a solvent stripping column to remove the water and the extract stream is passed to a solvent distillation column from which, in a first step, a mixture (A) comprising water and solvent is separated off at the top and a mixture (B) comprising acetic acid, formic acid and high boilers is separated off at the bottom, the mixture (B) is, after the formic acid has been separated off in a column which may be equipped with a side offtake, subsequently separated into pure acetic acid and high boilers in an acetic acid distillation column, and the mixture (A) is passed to a phase separator and the aqueous phase containing residual solvent is returned to the solvent stripping column and the organic phase is recirculated to the extractor.

A further preferred method is extraction by means of a solvent, preferably one or more compounds selected from the group consisting of ethers, esters, ketones and alcohols, particularly preferably one or more compounds selected from the group consisting of methyl tert-butyl ether, diisopropyl ether, ethyl butyl ether, ethyl acetate and isopropyl acetate, in a circulation process, wherein the raffinate stream containing the major part of the water is fed to a solvent stripping column to remove the water and the extract stream is passed to a solvent distillation column from which, in a first step, a mixture (A) containing the major part of the solvent is separated off at the top, a mixture (B) comprising formic acid, water and solvent is taken off at a side offtake and a mixture (C) comprising acetic acid and high boilers is separated off at the bottom, and the mixture (B) is passed to a formic acid distillation column for further work-up and the mixture (C) is passed to an acetic acid distillation column, the pure acetic acid is subsequently isolated via the top of the acetic acid distillation column, the pure formic acid is isolated at the bottom of the formic acid distillation column and a mixture of solvent and water is taken off at the top of the formic acid distillation column and is, together with the mixture (A) after the water has been separated off, recirculated to the extractor.

A further preferred method is extraction by means of a solvent, preferably one or more compounds selected from the group consisting of ethers, esters, ketones, hydrocarbons and alcohols, particularly preferably one or more compounds selected from the group consisting of methyl tert-butyl ether, diisopropyl ether, di-n-propyl ether, ethyl butyl ether, ethyl acetate and isopropyl acetate, in a circulation process, wherein the raffinate stream containing the major part of the water is fed to a solvent stripping column to remove the water and the extract stream is passed to a solvent distillation column from which, in a first step, a mixture (A) comprising water and solvent is separated off at the top and a mixture (B) comprising acetic acid, formic acid and high boilers is separated off at the bottom, the mixture (B) is, after the formic acid has been separated off in a column using an auxiliary in the manner of an azeotropic distillation, subsequently separated into pure acetic acid and high boilers in an acetic acid distillation column, and the mixture (A) is passed to a phase separator and the resulting aqueous phase containing residual solvent is returned to the solvent stripping column and the organic phase is recirculated to the extractor.

In the case of very high acetic acid concentrations in the crude acid, processes which are uncomplicated in terms of apparatus, e.g. azeotropic rectification, are more favorable for dewatering.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the present drawings wherein similar reference characters denote similar elements throughout the several views.

DETAILED DESCRIPTION OF PREFERRED EMBODIMENTS

Figure 1:
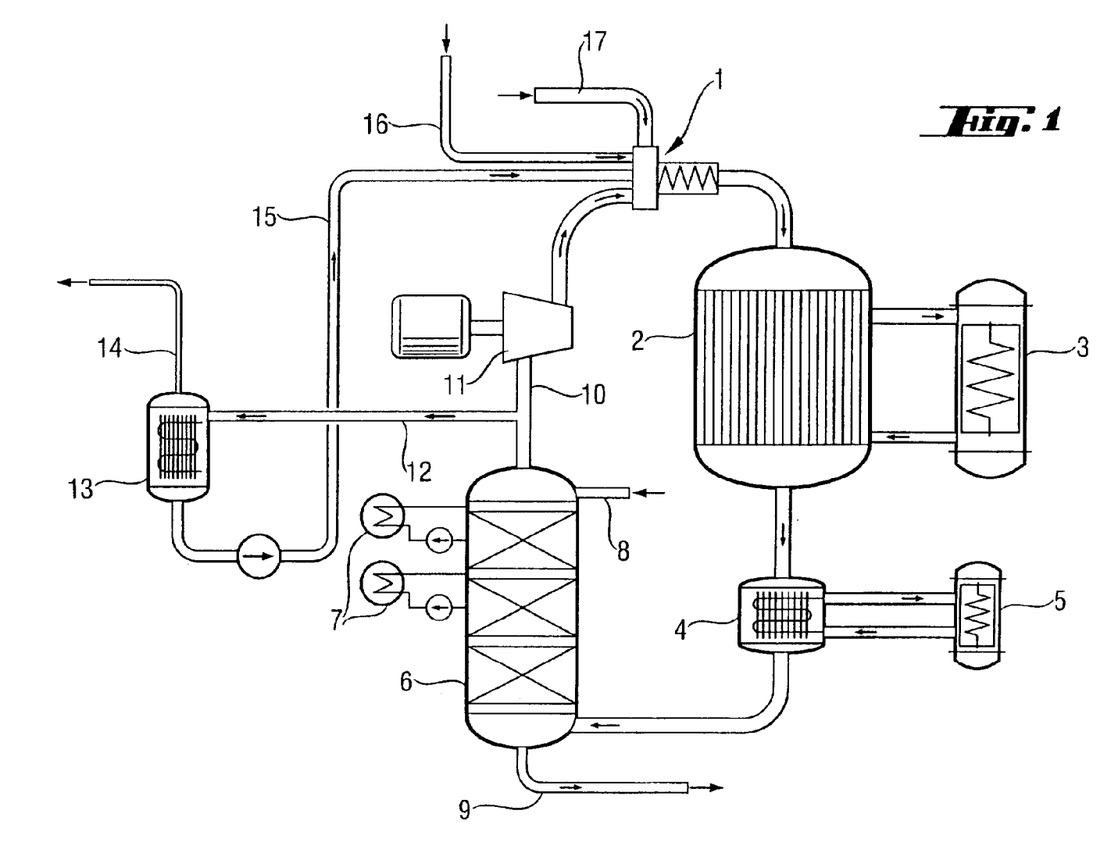
FIG. 1 shows an apparatus for preparing saturated carboxylic acids having from one to four carbon atoms, in particular acetic acid, by gas-phase oxidation of 2-butanone by contacting a coated catalyst by the process of the invention with recirculation of all or part of the reactor outlet gas.

Turning now in detail to the drawings, FIG. 1 shows that the crude acid is separated off, preferably by means of a countercurrent absorption using a solvent. The preferred solvent is water. Here, oxygen (line 17) and 2-butanone are mixed with the recirculated gas stream in a mixing zone (1) and are fed together with this recirculated stream to the shell-and-tube reactor (2) which is cooled by means of a cooling circuit (3). The main part of the gas mixture leaving the reactor is passed through a gas cooler (4) which is cooled by means of a circulation cooler (5). The reaction gas is subsequently passed to an absorption column (6) which is equipped with one or more column coolers (7). At the uppermost column tray, a solvent, preferably water, is fed in through a pipe (8). In this absorption column, the crude acid is separated off by countercurrent scrubbing and conveyed via a pipe (9) to further work-ups. The remaining reaction gas is recirculated via a pipe (10) to the mixing zone by means of a circulating gas compressor (11).

Figure 2:
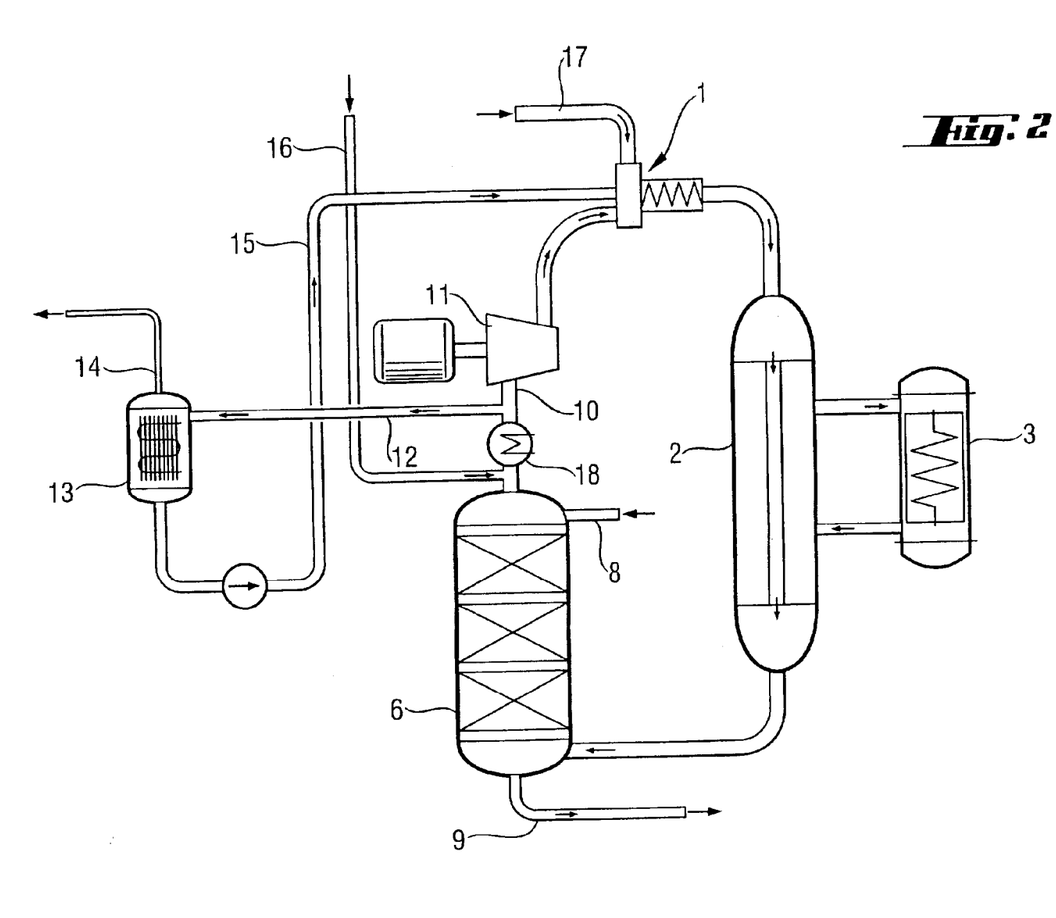
FIG. 2 shows an apparatus for preparing saturated carboxylic acids having from one to four carbon atoms, in particular acetic acid, by gas-phase oxidation of 2-butanone by contacting a coated catalyst by the process of the invention with recirculation of all or part of the reactor outlet gas.

The apparatus and the process can also be configured so that the carbon-containing starting material (2-butanone) is fed via line (16) not to the mixing nozzle but into the circuit at a point upstream of a cooling apparatus (18) (FIG. 2). To maintain steady-state conditions in the reaction circuit, a small offgas stream is taken off via line (12) and cooled in the offgas cooler (13), with the condensate obtained being recirculated via line (15) to the reactor inlet. The offgas stream taken off via line (14) comprises predominantly carbon oxides and residual combustible hydrocarbons and can be passed to thermal utilization, for example offgas combustion, utilization as material or some other offgas treatment.

The following examples serve to illustrate the invention.

The selectivity [in mol %] was calculated as follows:

Acetic acid selectivity based on 2-butanone conversion (mol %)=(((mol/h of acetic acid in the crude acid)/2)/(mol/h of 2-butanone reacted)×100

Formic acid selectivity based on 2-butanone conversion (mol %)=(((mol/h of formic acid in the crude acid)/4)/(mol/h of 2-butanone reacted)×100

Catalysts Used in the Examples:

Catalyst I: The catalyst used was produced by a method analogous to that of DE-A 19649426; the active composition consists of oxides of titanium, vanadium, molybdenum and antimony and has the empirical formula $Ti_aV_bMo_cSb_dO_e$ (a: 256; b: 27; c: 4; d: 13; e: 611) and is applied in an amount of 14.4% by weight plus 1.6% by weight of graphite, based on the weight of the support, to steatite rings having an external diameter of 7 mm, an internal diameter of 4 mm and a height of 4 mm.

Catalyst II: The catalyst used was produced by a method analogous to that of DE-A 19649426; the active composition consists of oxides of titanium, vanadium, molybdenum and antimony and has the empirical formula $Ti_aV_bMo_cSb_dO_e$ (a:

91; b: 7; c: 1; d: 3; e: 207) and is applied in an amount of 14.4% by weight plus 1.6% by weight of graphite, based on the weight of the support, to notched steatite rings similar to those described in EP 1108470 and having an external diameter of 7.3 mm, an internal diameter of 4.1 mm and a height of 4 mm, with two notches having a width of 1.4 mm and a depth of 2 mm on both the upper side and the underside.

The experiments were carried out in an apparatus corresponding to FIG. 2 comprising a single-tube reactor whose reaction tube had an internal diameter of 19 mm and an absorption column containing structured packing and having an internal diameter of 43 mm and a packing height of 3240 mm and provided with a thermostated top section condenser as column cooler.

COMPARATIVE EXAMPLE 1

Oxidation of $C_4$ Mixtures, Low n-butene Content

A reactor having an internal reaction tube diameter of 19 mm was charged with a catalyst of type I to a fill height of 3200 mm. The oxygen content at the reactor inlet was automatically regulated to 8% by volume. As reaction feed, 160 g/h of $C_4$ mixture containing 46% by weight of 1-butene, 20% by weight of n-butane, 13% by weight of t-2-butene, 9% by weight of c-2-butene, 4% by weight of i-butene and 8% by weight of i-butane were fed in. The circulating gas flow was set so that the reactor had a circulating gas flow of 13 000 g/h in steady-state operation. The reactor was operated at a pressure of $11 \times 10^5$ Pa and a coolant temperature of 195° C. The acids were separated off from the reaction gas by absorption using 1000 g/h of water (introduced at the top) in an absorber provided with structured packing and having an internal diameter of 43 mm and a packing height of 3240 mm at a temperature at the top of the absorber of 130° C.

Under these conditions, a butene conversion of 97% and a butane conversion of 47% were achieved. The acetic acid selectivity based on the total $C_4$ conversion was 53 mol %, and the formic acid selectivity based on the total $C_4$ conversion was 10 mol %. The volume-specific acetic acid productivity was 180 g/lh. The crude acid contained 86% by weight of water.

COMPARATIVE EXAMPLE 2

Oxidation of $C_4$ Mixtures, High n-butene Content

A reactor having an internal reaction tube diameter of 19 mm was charged with a catalyst of type I to a fill height of 3000 mm. The oxygen content at the reactor inlet was automatically regulated to 8% by volume. As reaction feed, 140 g/h of $C_4$ mixture containing 71% by weight of 1-butene, 11% by weight of n-butane, 8% by weight of t-2-butene, 5% by weight of c-2-butene, 2% by weight of i-butene and 3% by weight of i-butane were fed in. The circulating gas flow was set so that the reactor had a circulating gas flow of 13 000 g/h in steady-state operation. The reactor was operated at a pressure of $11 \times 10^5$ Pa and a coolant temperature of 190° C. The acids were separated off from the reaction gas by absorption using 640 g/h of water (introduced at the top) in an absorber provided with structured packing and having an internal diameter of 43 mm and a packing height of 3240 mm at a temperature at the top of the absorber of 130° C.

Under these conditions, a butene conversion of 96% and a butane conversion of 66% were achieved. The acetic acid selectivity based on the total $C_4$ conversion was 60 mol %, and the formic acid selectivity based on the total $C_4$ conversion was 13 mol %. The volume-specific acetic acid productivity was 190 g/lh. The crude acid contained 76% by weight of water.

EXAMPLE 1

Oxidation of 2-butanone (Methyl Ethyl Ketone)

A reactor having an internal reaction tube diameter of 19 mm was charged with a catalyst of type I to a fill height of 3200 mm. The oxygen content at the reactor inlet was automatically regulated to 8% by volume. As reaction feed, 340 g/h of 2-butanone were fed in. The circulating gas flow was set so that the reactor had a circulating gas flow of 18 000 g/h in steady-state operation. The reactor was operated at a pressure of $11 \times 10^5$ Pa and a coolant temperature of 185° C. The acids were separated off from the reaction gas by absorption using 1500 g/h of water (introduced at the top) in an absorber provided with structured packing and having an internal diameter of 43 mm and a packing height of 3240 mm at a temperature at the top of the absorber of 130° C.

Under these conditions, a 2-butanone conversion of 99.9% was achieved. The acetic acid selectivity based on the 2-butanone conversion was 89 mol %, and the formic acid selectivity based on the 2-butanone conversion was 5 mol %. The volume-specific acetic acid productivity was 550 g/lh. The crude acid contained 77% by weight of water.

EXAMPLE 2

Oxidation of 2-butanone (Methyl Ethyl Ketone)

A reactor having an internal reaction tube diameter of 19 mm was charged with a catalyst of type II to a fill height of 3000 mm. The oxygen content at the reactor inlet was automatically regulated to 8% by volume. As reaction feed, 230 g/h of 2-butanone were fed in. The circulating gas flow was set so that the reactor had a circulating gas flow of 13 000 g/h in steady-state operation. The reactor was operated at a pressure of $11 \times 10^5$ Pa and a coolant temperature of 188° C.

The acids were separated off from the reaction gas by absorption using 410 g/h of water (introduced at the top) in an absorber provided with structured packing and having an internal diameter of 43 mm and a packing height of 3240 mm at a temperature at the top of the absorber of 130° C.

Under these conditions, a 2-butanone conversion of 99.8% was achieved. The acetic acid selectivity based on the 2-butanone conversion was 83 mol %, and the formic acid selectivity based on the 2-butanone conversion was 5 mol %. The volume-specific acetic acid productivity was 370 g/lh. The crude acid contained 52% by weight of water.

EXAMPLES 3–9

Oxidation of 2-butanone (Methyl Ethyl Ketone)

Examples 3–9 were carried out using a method analogous to Example 2 under the conditions specified in Table 1 and gave the results reported in the Table.

EXAMPLE 10

Oxidation of 2-butanone (Methyl Ethyl Ketone)

A reactor having an internal reaction tube diameter of 19 mm was charged with a catalyst of type II to a fill height of 1200 mm. The oxygen content at the reactor inlet was automatically regulated to 8% by volume. As reaction feed, 250 g/h of 2-butanone were fed in. The circulating gas flow was set so that the reactor had a circulating gas flow of 11 000 g/h in steady-state operation. The reactor was operated at a pressure of $11 \times 10^5$ Pa and a coolant temperature of 173° C.

The acids were separated off from the reaction gas by absorption using 1500 g/h of water (introduced at the top) in an absorber provided with structured packing and having an internal diameter of 43 mm and a packing height of 3240 mm at a temperature at the top of the absorber of 130° C.

Under these conditions, a 2-butanone conversion of 99.5% was achieved. The acetic acid selectivity based on the 2-butanone conversion was 83 mol %, and the formic acid selectivity based on the 2-butanone conversion was 4 mol %. The volume-specific acetic acid productivity was 1025 g/lh. The crude acid contained 79% by weight of water.

EXAMPLE 11

Oxidation of 2-butanone (Methyl Ethyl Ketone)

A reactor having an internal reaction tube diameter of 19 mm was charged with a catalyst of type II to a fill height of 1200 mm. The oxygen content at the reactor inlet was automatically regulated to 8% by volume. As reaction feed, 240 g/h of 2-butanone were fed in. The circulating gas flow was set so that the reactor had a circulating gas flow of 11 000 g/h in steady-state operation. The reactor was operated at a pressure of $11 \times 10^5$ Pa and a coolant temperature of 185° C.

The acids were separated off from the reaction gas by absorption using 30 g/h of water (introduced at the top) in an absorber provided with structured packing and having an internal diameter of 43 mm and a packing height of 3240 mm at a temperature at the top of the absorber of 95° C.

Under these conditions, a 2-butanone conversion of 97.5% was achieved. The acetic acid selectivity based on the 2-butanone conversion was 78 mol %, and the formic acid selectivity based on the 2-butanone conversion was 2 mol %. The volume-specific acetic acid productivity was 890 g/lh. The crude acid contained 16% by weight of water.

TABLE 1

| Example No. | Catalyst | Diameter × fill height [mm] | Pressure × $10^5$ [Pa] | Coolant temperature [° C.] | Circulating gas flow [kg/h] | C feed [g/h] *R2 | Absorber water [g/h] |
|---|---|---|---|---|---|---|---|
| CE 1 | I | 19 × 3200 | 11 | 195 | 13 | 160'1 | 1000 |
| CE 2 | I | 19 × 3000 | 11 | 190 | 13 | 140'2 | 640 |
| 1 | I | 19 × 3200 | 11 | 185 | 18 | 340 | 1500 |
| 2 | II | 19 × 3000 | 11 | 188 | 13 | 230 | 410 |
| 3 | II | 19 × 3000 | 11 | 194 | 13 | 180 | 415 |
| 4 | II | 19 × 3000 | 11 | 189 | 14 | 220 | 205 |
| 5 | II | 19 × 3000 | 11 | 188 | 13 | 245 | 105 |
| 6 | II | 19 × 3000 | 11 | 189 | 11 | 245 | 50 |
| 7 | II | 19 × 3000 | 11 | 191 | 11 | 245 | 40 |
| 8 | II | 19 × 3000 | 11 | 182 | 11 | 245 | 0 |
| 9 | II | 19 × 3000 | 9 | 183 | 10 | 250 | 0 |
| 10 | II | 19 × 1200 | 11 | 173 | 11 | 250 | 1500 |
| 11 | II | 19 × 1200 | 11 | 185 | 11 | 240 | 30 |

| Example No. | Temp. at top of absorber [° C.] | Conversion [%] *butene/butane | Selectivity [mol %] AcOH | Selectivity [mol %] HCOOH | Productivity [g/lh] AcOH | Crude acid [% by weight] Water |
|---|---|---|---|---|---|---|
| CE 1 | 130 | 97/47* | 53 | 10 | 180 | 86 |
| CE 2 | 130 | 96/66* | 60 | 13 | 190 | 76 |
| 1 | 130 | 99.9 | 89 | 5 | 550 | 77 |
| 2 | 130 | 99.8 | 83 | 5 | 370 | 52 |
| 3 | 130 | 99.9 | 85 | 5 | 300 | 60 |
| 4 | 130 | 99.6 | 82 | 4 | 350 | 36 |
| 5 | 130 | 99.3 | 82 | 4 | 390 | 25 |
| 6 | 109 | 99.7 | 84 | 3 | 400 | 17 |
| 7 | 106 | 99.5 | 82 | 3 | 390 | 14 |
| 8 | 90 | 98.7 | 82 | 3 | 390 | 9 |
| 9 | 89 | 98.4 | 79 | 2 | 380 | 8 |
| 10 | 130 | 99.5 | 83 | 4 | 1025 | 79 |
| 11 | 95 | 97.5 | 78 | 2 | 890 | 16 |

$C_4$-1: 46% by weight of 1-butene, 20% by weight of n-butane, 13% by weight of t-2-butene, 9% by weight of c-2-butene, 4% by weight of i-butene, 8% by weight of i-butane.

$C_4$-2: 71% by weight of 1-butene, 11% by weight of n-butane, 8% by weight of t-2-butene, 5% by weight of c-2-butene, 2% by weight of i-butene, 3% by weight of i-butane.

Accordingly, while a few embodiments of the present invention have been shown and described, it is to be understood that many changes and modifications may be made thereunto without departing from the spirit and scope of the invention as defined in the appended claims.

What is claimed is:

1. A process for preparing saturated carboxylic acid having from one to four carbon atoms by gas-phase oxidation, which comprises reacting 2-butanone with oxygen by contact with a coated catalyst, said coated catalyst comprising an inert nonporous support body having an external surface and a catalytically active mixed oxide composition comprising
(a) at least one oxide selected from the group consisting of titanium dioxide, zirconium dioxide, tin dioxide an aluminum oxide, and
(b) from 0.1% to 1.5% by weight, based on the weight of the component (a) and per $in^2/g$ of specific surface area of the component (a), of vanadium pentoxide,
applied to the external surface of the support body, and
said 2-butanone being selected from the group consisting of
(1) pure 2-butanone as feedstock as carbon source; and
(2) 2-butanone-containing primary product mixtures obtained in preparation of 2-butanone are used directly as feedstocks.

2. The process as claimed in claim 1,
wherein the catalytically active mixed oxide composition of the coated catalyst further comprises, as part of component (a), at least one oxide of a metal selected from the group consisting of boron, silicon, hafnium, niobium, tungsten, lanthanum and cerium, in an amount of from 1% to 30% by weight, base on the total weight of the component (a).

3. The process as claimed in claim 1,
wherein, in the catalytically active mixed oxide composition of the coated catalyst, part of the vanadium pentoxide of component (b) is replaced by at least one oxide of a metal selected from the group consisting of molybdenum, chromium, antimony, an alkali metal, an alkaline earth metal, an element of main group 5 and 6 of the Periodic Table of the Elements and a transition metal and it is present as an additional component (b).

4. The process as claimed in claim 1,
wherein at least one layer of the catalytically mixed oxide composition is present in the coated catalyst.

5. The process as claimed in claim 1,
wherein the coated catalyst has a plurality of layers of which an inner layer comprises only component (a) and an outer layer comprises components (a) and (b).

6. The process as claimed in claim 1,
wherein the coated catalyst has a plurality of layers of which an inner layer and an outer layer each comprises components (a) and (b) and a higher specific surface area of the component (a) is selected for the inner layer than for the outer layer.

7. The process as claimed in claim 1,
wherein the inert support body of the coated catalyst has a shape of a hollow cylinder which has at least one notch on an upper end face and a lower end face of hollow cylinder walls, so that an interior space of the hollow cylinder is joined to spaces surrounding the hollow cylinder via openings.

8. The process as claimed in claim 1,
wherein a gas mixture comprising from 1% to 35% by volume of oxygen, from 0.3% to 10% by volume of 2-butanone, from 5% to 80% by volume of water vapor and from 0% to 90% by volume of carbon oxides, so that the percentages by volume of the individual constituents of the gas mixture in each case add up to 100%, is reacted by contacting the coated catalyst at a temperature of from 100° C. to 400° C. and a superatmospheric pressure of from $1.2 \times 10^5$ to $51 \times 10^5$ Pa; and wherein each percent by volume is based upon the total volume of the gas mixture.

9. The process as claimed in claim 1, further comprising a reactor outlet gas; and
wherein said reactor outlet gas is partly recirculated in a reaction gas circuit which is configured so that part of organic acids formed in the gas-phase oxidation are separated off from the reactor outlet gas so that the proportion of acids in part of the reactor outlet gas which is recirculated is reduced to from 0.01% to 12% by volume; and
the percent by volume is based upon the total volume of the reactor outlet gas.

10. The process as claimed in claim 9,
wherein the acids are separated off down to a specified residual acid content from 60–99.8% by weight of the reactor outlet gas and this part of the reactor outlet gas is subsequently recirculated to the reactor; and
the percent by volume is based upon the total volume of the reactor outlet gas.

11. The process as claimed in claim 10,
wherein the acids are separated off down to the specified residual content from the reactor outlet gas immediately after it leaves the reactor and the reactor outlet gas which has been treated in this way is wholly or partly recirculated to the reactor.

12. The process as claimed in claim 1, further comprising a recirculated gas stream; and
wherein the mass flow of said recirculated gas stream is from 1 to 100 times mass flow of a fresh feed introduced.

13. The process as claimed in claim 11,
wherein the reactor outlet gas is partly recirculated in a reaction gas circuit to and from the reactor, and the acid concentration in the recirculated part is reduced by means of a separation step, wherein the crude acid is separated of from the reactor outlet gas by a means selected from the group consisting of a countercurrent scrub, a cocurrent scrub, a cross-stream scrub, quench cooling, partial condensation and a combination thereof.

14. The process as claimed in claim 1, further comprising
separating and purifying an aqueous mixture of main components comprising acetic acid, formic acid and high boilers by extraction in an extractor by means of a solvent in a circulation process, where a raffinate stream from the extractor containing a major part of water is fed to a solvent stripping column to remove the water; and
passing an extract stream to a solvent distillation column from which, in a first step, a mixture (A) containing a major part of the solvent is separated off at the top, a mixture (B) comprising formic acid, water and solvent is taken off at a side off take and a mixture (C) comprising acetic acid and high boilers is separated off at a bottom; and
passing the mixture (B) to a formic acid distillation column for further work-up and passing the mixture (C) to an acetic acid distillation column, pure acetic acid is subsequently isolated via a top of the acetic acid distillation column; and
isolating pure formic acid at a bottom of the acid distillation column and a mixture of solvent and water is taken off at the top of the formic acid distillation column and is, together with the mixture (A) after the water has been separated off, recirculated to the extractor.

15. The process as claimed in claim 1, further comprising separating and purifying an aqueous mixture of main components comprising acetic acid, formic acid and high boilers by extraction in an extractor by means of a solvent in a circulation process, where a raffinate stream from the extractor containing a major part of water is fed to a solvent stripping column to remove the water;

passing an extract stream to a solvent distillation column from which, in a first step, a mixture (A) comprising water and solvent is separated off at a top and a mixture (B) comprising acetic acid, formic acid and high boilers is separated off at a bottom;

the mixture (B) is, after the formic acid has been separated off in a column which is equipped with a side offtake, subsequently separated into pure acetic acid and high boilers in an acetic acid distillation column; and passing the mixture (A) to a phase separator and a aqueous phase containing residual solvent is returned to the solvent stripping column and the organic phase is recirculated to the extractor.

16. The process as claimed in claim 1, further comprising separating and purifying an aqueous mixture of main components comprising acetic acid, formic acid and high boilers by extraction in an extractor by means of a solvent in a circulation process, where a raffinate stream from the extractor containing a major part of water is fed to a solvent stripping column to remove the water;

passing an extract stream to a solvent distillation column from which, in a first step, a mixture (A) comprising water and solvent is separated off at a top and a mixture (B) comprising acetic acid, formic acid and high boilers is separated off at a bottom;

the mixture (B) is, after the formic acid has been separated off in a column using an azeotropic distillation, subsequently separated into pure acetic acid and high boilers in an acetic acid distillation column; and and passing the mixture (A) to a phase separator and a resulting aqueous phase containing residual solvent is returned to the solvent stripping column and the organic phase is recirculated to the extractor.

17. The process as claimed in claim 1, wherein dewatering of an aqueous mixture of main components comprising acetic acid, formic acid and high boilers obtained is carried out by means of an azeotropic rectification.

18. The process as claimed in claim 1, wherein 2-butanone-containing primary product mixtures obtained in preparation of 2-butanone are used directly as feedstocks.

19. The process as claimed in claim 1, wherein water/2-butanone azeotropes obtained as primary product mixtures in direct oxidation of 2-butenes over palladium catalysts are used directly as feedstocks.

20. The process as claimed in claim 1, wherein said 2-butanone is pure 2-butanone.

* * * * *